US008668699B2

(12) United States Patent
Thomas et al.

(10) Patent No.: US 8,668,699 B2
(45) Date of Patent: Mar. 11, 2014

(54) MULTI-FUNCTION ORTHOPEDIC INSTRUMENT

(75) Inventors: Bradley G. Thomas, Memphis, TN (US); Eric Steven Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1734 days.

(21) Appl. No.: 11/105,657

(22) Filed: Apr. 14, 2005

(65) Prior Publication Data
US 2006/0235427 A1 Oct. 19, 2006

(51) Int. Cl.
*A61F 2/46* (2006.01)

(52) U.S. Cl.
USPC ....................................... 606/86 R

(58) Field of Classification Search
USPC .............. 606/86, 99, 102, 105, 86 R, 86 A, 606/205–210; 7/125–131; 81/3.6, 3.7, 9.4, 81/9.44, 427.5, 303–427
See application file for complete search history.

(56) References Cited

U.S. PATENT DOCUMENTS

| | | | |
|---|---|---|---|
| 2,631,585 A * | 3/1953 | Siebrandt | 606/86 |
| 2,668,464 A * | 2/1954 | Paules | 30/91.2 |
| 3,733,626 A * | 5/1973 | Allen | 7/107 |
| 3,890,858 A * | 6/1975 | Lawson et al. | 30/90.1 |
| 4,050,464 A * | 9/1977 | Hall | 606/61 |
| 4,457,306 A * | 7/1984 | Borzone | 606/1 |
| 4,474,046 A * | 10/1984 | Cook | 72/409.16 |
| 5,084,935 A * | 2/1992 | Kalthoff | 7/132 |
| 5,280,659 A * | 1/1994 | Park | 7/128 |
| 5,314,431 A * | 5/1994 | Graziano | 606/101 |
| 5,360,431 A | 11/1994 | Puno et al. | |
| 5,389,099 A | 2/1995 | Hartmeister et al. | |
| 5,474,555 A | 12/1995 | Puno et al. | |
| 5,490,409 A * | 2/1996 | Weber | 72/458 |
| 5,545,168 A * | 8/1996 | Burke | 606/74 |
| 5,624,442 A | 4/1997 | Mellinger et al. | |
| 5,697,933 A * | 12/1997 | Gundlapalli et al. | 606/96 |
| 5,893,185 A * | 4/1999 | Okrepkie et al. | 7/107 |
| 6,146,386 A | 11/2000 | Blackman et al. | |
| 6,497,133 B1 * | 12/2002 | Rose | 72/388 |
| 6,551,316 B1 * | 4/2003 | Rinner et al. | 606/57 |

(Continued)

FOREIGN PATENT DOCUMENTS

EP 1 470 792 10/2004

OTHER PUBLICATIONS

Medtronic Sofamor Danek Product Catalog, 2000, pp. A-15, A-40 and A-48.

*Primary Examiner* — Mary Hoffman
*Assistant Examiner* — Tara Carter (57) ABSTRACT

Instrumentation is disclosed for use in orthopedic surgery that is capable of use as a compressor, a distractor, and a rod bender. Two pivoting arms have ends that can be used to compress implants, bones, or bone fragments together or to distract such items apart. In orthopedic surgery in which a rod, bar, plate, or other support is used, the instrument may be used to introduce bends into such supports so that the orthopedic structures (e.g. vertebrae) remain in a desired portion. Additional features are provided that permit verification of size of implantable items and packing of material in intervertebral spacers and similar devices.

30 Claims, 8 Drawing Sheets

(56) References Cited

U.S. PATENT DOCUMENTS

| | | | |
|---|---|---|---|
| 6,726,692 B2 * | 4/2004 | Bette | 606/99 |
| 6,739,068 B1 * | 5/2004 | Rinner | 33/783 |
| 7,171,712 B2 * | 2/2007 | Konen | 7/107 |
| 2002/0072752 A1 * | 6/2002 | Zucherman et al. | 606/99 |
| 2004/0063521 A1 * | 4/2004 | Oister et al. | 473/476 |
| 2004/0267279 A1 * | 12/2004 | Casutt et al. | 606/104 |
| 2005/0049712 A1 * | 3/2005 | Ondrla et al. | 623/22.12 |
| 2006/0111726 A1 * | 5/2006 | Felt et al. | 606/86 |

\* cited by examiner

MULTI-FUNCTION ORTHOPEDIC INSTRUMENT

Instrumentation for use in orthopedic treatments is disclosed. In particular, this disclosure relates to instruments for configuring and positioning orthopedic implants with respect to each other and/or parts of the human body.

BACKGROUND

In the field of orthopedic treatment and surgery, implants are frequently attached to bones or other tissue so as to provide treatment or correction for orthopedic injuries or abnormal conditions. For example, in treatment of spinal abnormalities such as scoliosis, implants such as bone hooks or bone screws may be attached to or implanted within individual vertebrae. Following adjustment of the vertebrae to a desired curvature or position, such bone hooks or screws may be immobilized with respect to each other by way of a rod, bar, plate, or other relatively rigid structure. The rod or other structure maintains the bones, by way of the implants, in the desired position, supporting the patient's anatomy in at least some approximation of normalcy.

Commonly, tools are provided to assist the surgeon in completing the repositioning and immobilization or control of the repositioned vertebrae or other bones or tissue. In a spinal surgery, for example, once the spinal hooks, screws, or clamps are attached to vertebrae, a trial may be provided to compress (move together) or distract (move apart) the implants, and therefore the vertebrae to which they are attached. A compressor tool, for example, may have end portions that are spaced relatively distant from each other and configured to attach to a portion of a spinal implant. When such end portions are brought together, the implants and their respective vertebrae are brought together, compressing the vertebrae or reducing the space between them. Conversely, in a distractor tool two end portions may be provided that are abutting, adjacent, or relatively close together and are configured to abut, connect, or attach to parts of such spinal implants. When the end portions are moved away from each other, they cause the implants and their respective vertebrae to be distracted, that is, moved apart.

Other tools are also known for orthopedic surgery. For example, in spinal corrective surgery a rod, bar, plate, or other connection between bone screws or other implants may include one or more bends, in order that the instrumented vertebrae be maintained in a particular relationship or curvature. If an orthopedic surgeon wishes to support or correct a spine portion which in a normal anatomy would include both kyphotic and lordotic, curvatures, for instance, the surgeon may wish to bend an initially substantially straight rod so that, it approximates both types of curvature. Accordingly, rod-bending tools, commonly known as "benders," have been developed.

Previously, tools for orthopedic surgery have had but one use. Thus, in order to have all treatment options available to an orthopedic surgeon, all the potentially necessary tools are provided to or available to the surgeon, even though the surgeon might not, in fact, need all such tools for the given patient. Frequently such tools are provided newly manufactured, despite the fact that they may not all be needed. The surgeon or his team is forced to look among the unnecessary tools for the necessary tool during the surgical procedure.

Accordingly, there is a need in the field for instrumentation that overcomes such inefficiencies.

DESCRIPTION OF THE ILLUSTRATED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated, as would normally occur to one skilled in the art to which the invention relates.

Referring now generally to the figures, there is shown an embodiment of an instrument 20 that is capable of performing multiple tasks for an orthopedic surgeon. In that embodiment, instrument 20 includes two substantially symmetrical elongated arms 22, 24. Arms 22, 24 are connected and pivotable at a medial point 26. In the illustrated embodiment, point 26 is generally on an inside potion of each of arms 22, 24. That is, in one embodiment a relatively interior portion of arm 22 is connected to a relatively interior portion of arm 24 in such a way that arms 22, 24 are connected to but pivotable with respect to each other.

Figure 1:
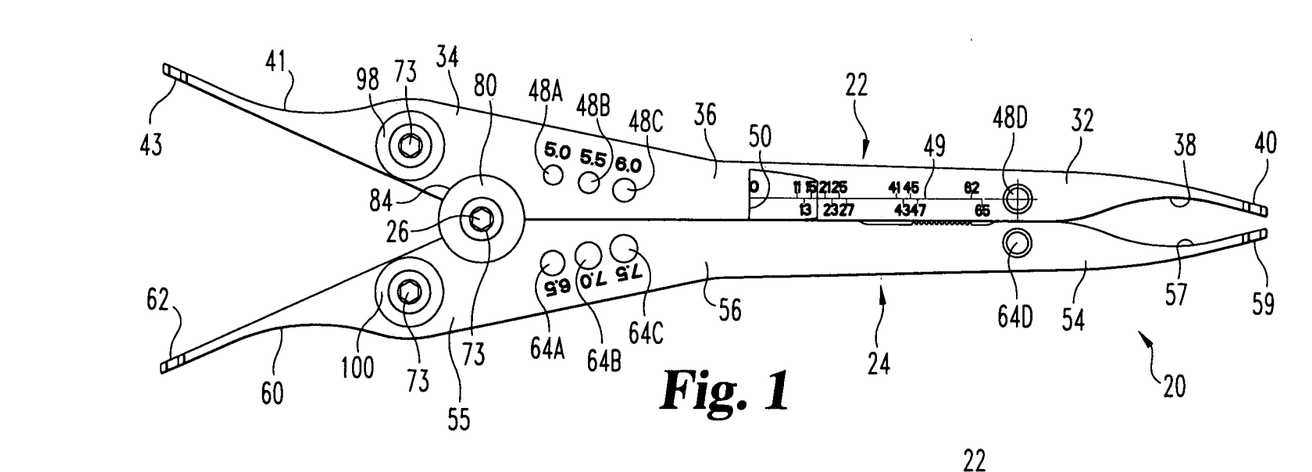
FIG. 1 is a top plan view of an embodiment of an instrument disclosed herein.
Figure 2:
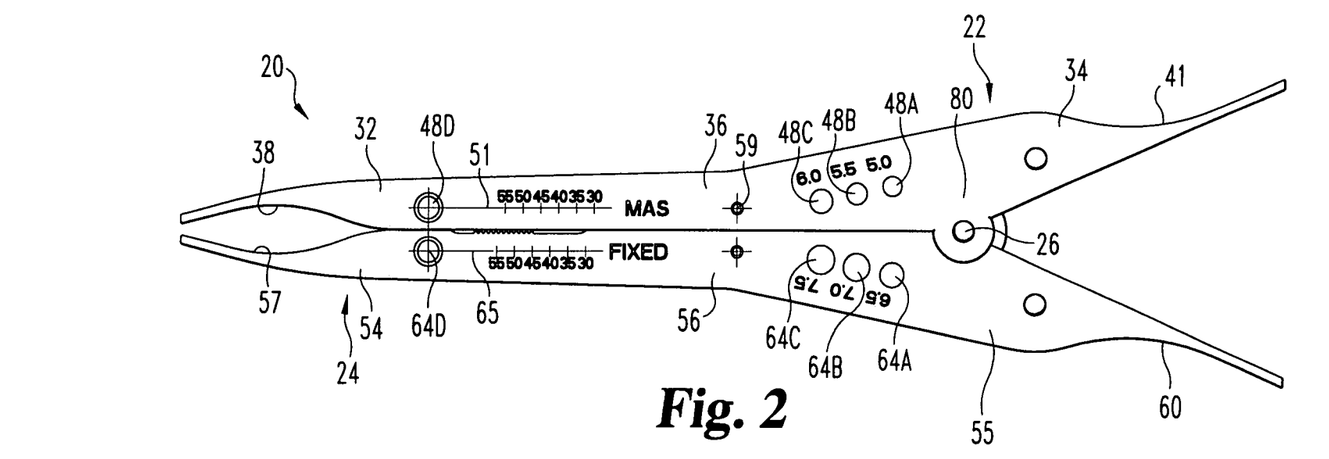
FIG. 2 is a bottom plan view of the embodiment shown in FIG. 1.
Figure 3:
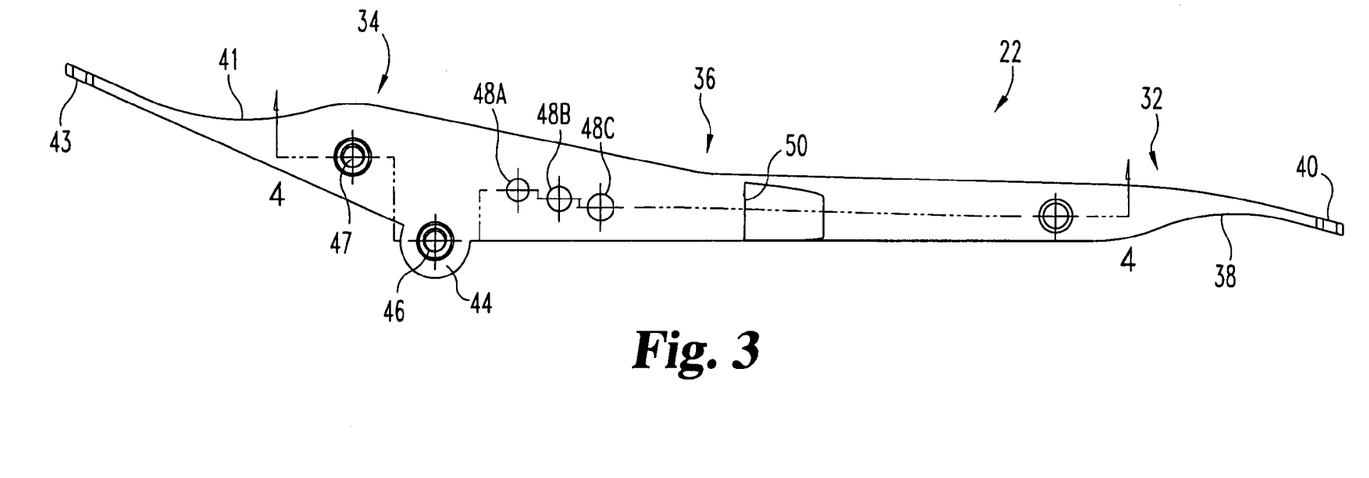
FIG. 3 is a top plan view of an embodiment of one aspect of the embodiment of the instrument shown in FIG. 1.
Figure 4:
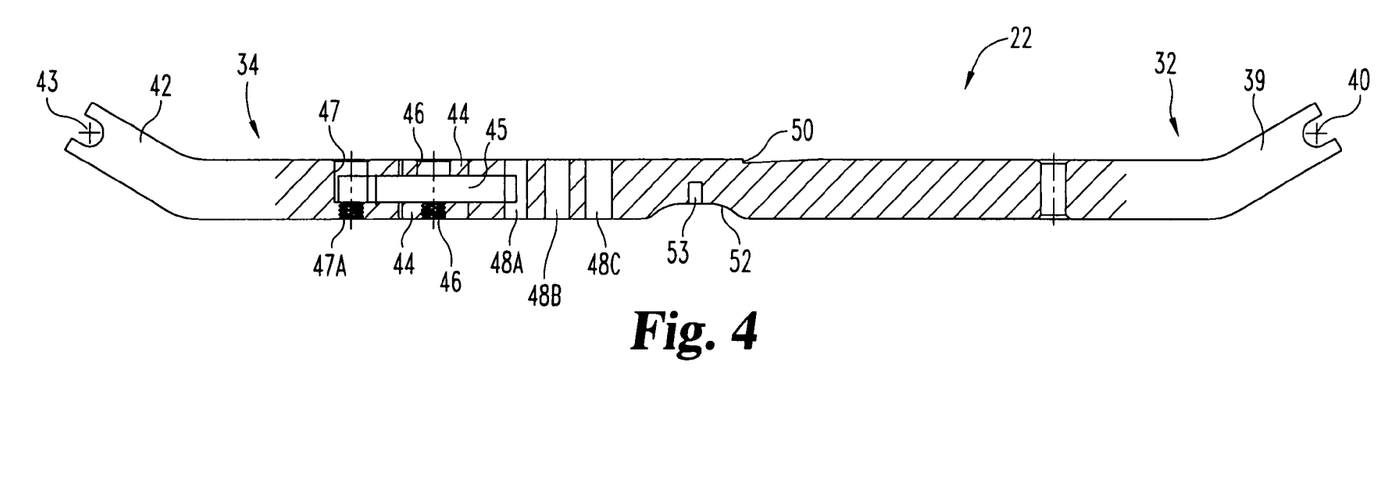
FIG. 4 is a partial cross-sectional view of the embodiment shown in FIG. 3, taken along the lines 4-4 in FIG. 3 and viewed in the direction of the arrows.
Figure 5:
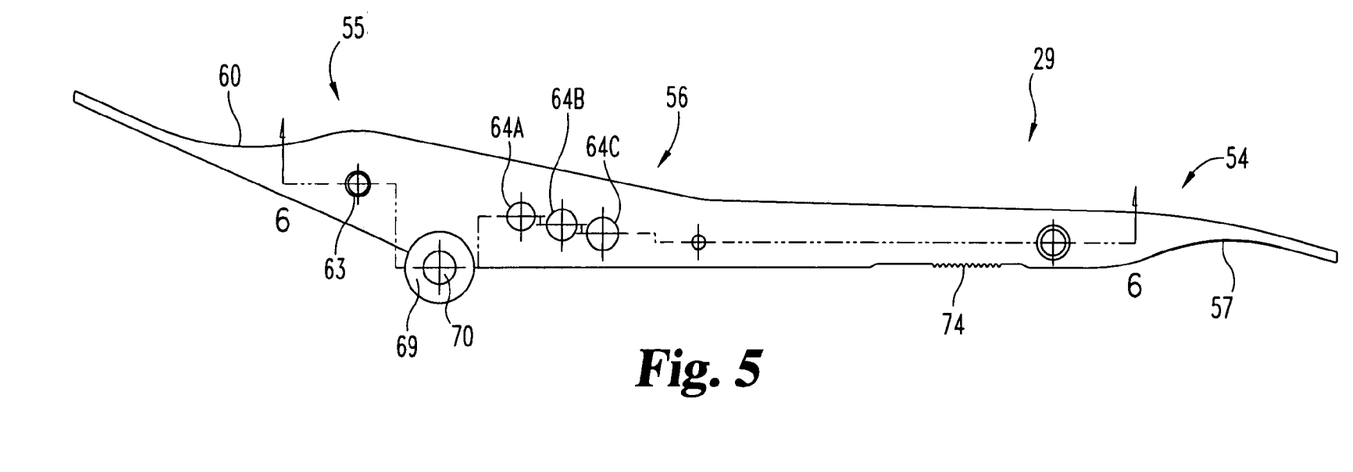
FIG. 5 is a bottom plan view of an embodiment of another aspect of the embodiment of the instrument shown in FIG. 1.
Figure 6:
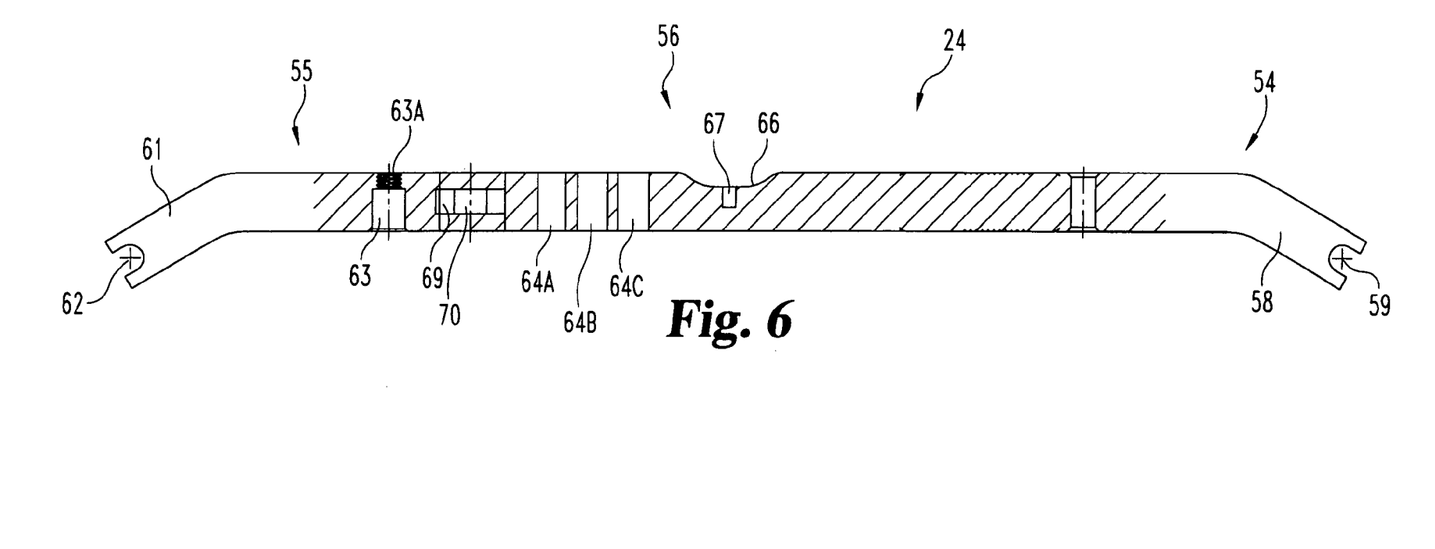
FIG. 6 is a partial cross-sectional view of the embodiment shown in FIG. 5, taken along the lines 6-6 in FIG. 5 and viewed in the direction of the arrows.
Figure 7A:
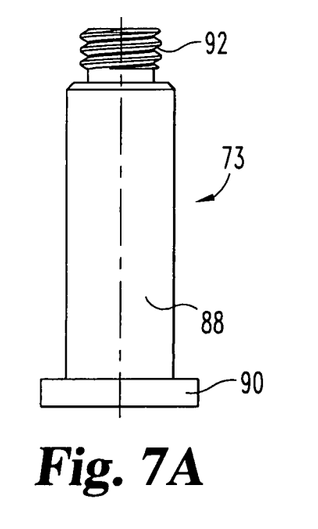
FIG. 7A is a side view of an embodiment of an axle used in the embodiment shown in FIG. 1.
Figure 7B:
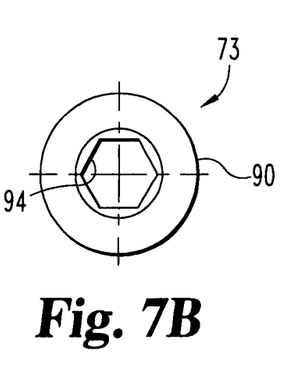
FIG. 7B is a top view of the embodiment shown in FIG. 7A.
Figure 8A:
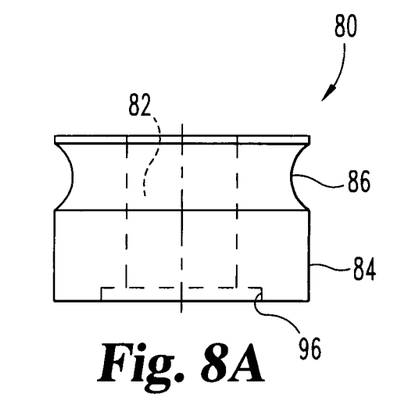
FIG. 8A is a side view of an embodiment of a disk used in the embodiment shown in FIG. 1.
Figure 8B:
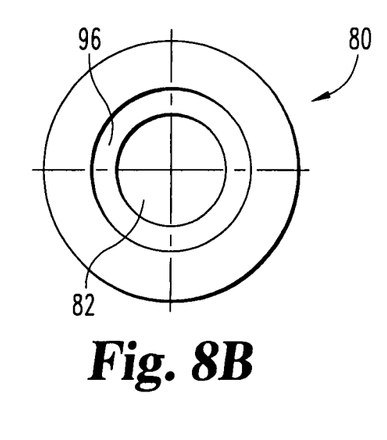
FIG. 8B is a top view of the embodiment shown in FIG. 8A.
Figure 9A:
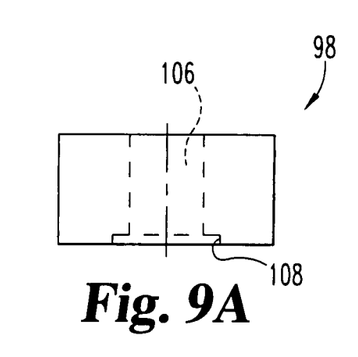
FIG. 9A is a side view of an embodiment of a disk used in the embodiment shown in FIG. 1.
Figure 9B:
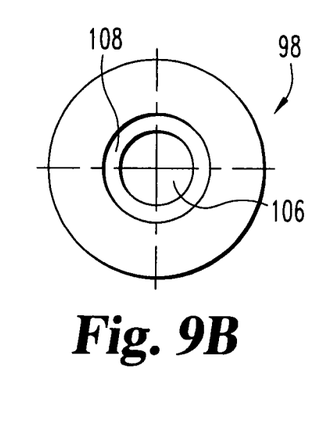
FIG. 9B is a top view of the embodiment shown in FIG. 9A.

Arm 22 includes a first end portion 32, a second end portion 34, and a medial portion 36. End portion 32 includes a curve in the illustrated embodiment, generally formed so that end portion 32 converges or curves toward arm 24 when arms 22 and 24 are attached or connected. End portion 32 also includes a relatively concave portion 38 on an inside portion of arm 22, e.g. generally facing arm 24 when arms 22 and 24 are connected. End portion 32 includes at least a part in the illustrated embodiment that is angled with respect to a plane of medial portion 36. As seen more clearly in FIG. 4, the illustrated embodiment of arm 22, when viewed from the side, includes a section 39 at least a portion of which is angled at about 150 degrees to medial portion 36. An opening or channel 40, which may be substantially U-shaped, is formed in end portion 32. As further explained below, opening 40 is preferably sized to accommodate a portion of a rod, bar, plate or other support member extending between implants such as a bone screws, bolts clamps or hooks.

End portion 34 of arm 22 diverges or is curved so as to point generally away from arm 24 when arms 22 and 24 are connected together. End portion 34 includes a concave surface 41 on an outside surface, e.g. generally pointing away from arm 24 when arms 22 and 24 are connected together. A section 42 of end portion 34, as seen from the side, may be angled with respect to medial portion 36 substantially in the same way as a section of end portion 32. Further, end portion 34, in the illustrated embodiment, includes an opening or channel 43, which in one embodiment is of approximately the same shape and dimension as opening 40 of end portion 32, and serves substantially the same purpose. It will be understood that the dimension and configuration of opening 43 may be different (e.g. larger or smaller) than opening 40.

Arm 22 includes a pair of flanges 44 that are substantially circular in the illustrated embodiment and separated by a gap or slot 45. Flanges 44 each have a hole 46, which are substantially concentric. One or both of holes 46 may be partially or completely threaded. In the embodiment illustrated in FIG. 4, the lower hole 46 is completely threaded, and the upper hole 46 is not threaded and has a diameter larger than that of the lower hole 46. Arm 22 also includes a hole 47, which in one embodiment has a threaded portion 47A.

Additionally, arm 22 may include one or more holes 48 therethrough. In the illustrated embodiment, holes 48A, 48B, 48C, and 48D are shown through arm 22. Holes 48A, 48B and 48C may be sized approximately equal to or slightly larger than the diameters of different size implants. For example, hole 48A may be sized to accommodate a 5.0 millimeter diameter implant (e.g. hole 48A may have a diameter slightly larger than 5.0 millimeters), hole 48B may be sized to accommodate a 5.5 millimeter diameter implant (e.g. hole 48B may have a diameter slightly larger than 5.5 millimeters), and hole 48C may be sized to accommodate a 6.0 millimeter diameter implant (e.g. hole 48C may have a diameter slightly larger than 6.0 millimeters). Hole 48D may be provided for bending large angles into support members. For example, a rod may be placed into hole 48D to a desired depth and bent over arm 22. For such use, one could disconnect arms 22 and 24 before using hole 48D to bend. Markings 49 may be placed on a side surface of arm 22 that would allow a measurement or verification of a length of a support member. A ledge 50 in arm 22 acts as a reference point, and the support member is placed against it. The length of the support can be determined or verified by reading the measurement from the gauge lines. In one embodiment, only lengths of supports supplied in a set or kit are shown on the gauge to avoid clutter or confusion. Additionally, lengths of relatively small implants used with a support can be determined or verified by using the gauge substantially as previously described.

Markings 51 may also be placed on an opposite side of arm 22 which may be used to determine or verify the length of an implant, in one particular instance a multi-axial screw. A hollow or indentation 52 is provided, in one embodiment, in which a hole 53 (which could house a pin or other reference marker) can be placed. The implant is placed in a hollow, e.g. a rounded seat portion is laid in hollow 52, and the length of the implant is read from or verified by reference to markings 51. If the implant includes a protrusion, then the protrusion could be fitted into or adjacent hole 53, and then the length can be read. If the implant has an appropriate hole, and a pin is in hole 53, then such hole in the implant can be placed over or adjacent the pin, and the length of the implant can be read or verified. Of course, it will be understood that other types of markings indicating measurements, configuration, or other information may be placed on arms 22 or 24.

Arm 24, in the illustrated embodiment, is substantially symmetric with arm 22. Arm 24 includes end portions 54 and 55 and a medial portion 56. End portion 54, in the illustrated embodiment, converges or curves generally inward toward arm 22 when arm 22 and 24 are connected with each other. A relatively concave surface 57 on an inside surface, e.g. generally facing arm 22, may be provided. At least a part 58 of end portion 54 is, in one embodiment, angled with respect to medial portion 56, and in one particular embodiment such angle may be about 150 degrees. An opening or channel 59, which may be substantially U-shaped, is placed in end portion 54. Opening 59 may be sized and configured to accommodate a rod, bar or other support member connecting implants. In a specific embodiment, opening 59 is sized and configured substantially the same as opening 40 of arm 22.

End portion 55, in the illustrated embodiment, is curved so as to diverge or point relatively away from arm 22 when arms 22 and 24 are connected together. A concave surface 60 is on an outside portion of arm 24, i.e., concave surface 60 generally faces away from arm 22 when arms 22 and 24 are connected together. At least a part 61 of end portion 52 may be relatively angled with respect to medial portion 56, which angle may be about 150 degrees. An opening or channel 62 is provided in end portion 55, which may be sized and configured to accommodate a support member that connects implants. In one particular embodiment, opening 62 is of substantially the same size and configuration as opening 46 of arm 22. A hole 63 is provided through arm 22, which in one embodiment has a threaded portion 63A.

Arm 24 may further include a series of holes 64 therethrough. In the illustrated embodiment, hole 64A, 64B, 64C, and 64D are shown through arm 24. Holes 64A, 64B and 64C may be sized approximately equal to or slightly larger than the diameters of different implants. For example, hole 64A may be sized to accommodate a 6.5 millimeter diameter implant (e.g. hole 64A may have a diameter slightly larger than 6.5 millimeters), hole 64B may be sized to accommodate a 7.0 millimeter diameter implant (e.g. hole 64B may have a diameter slightly larger than 7.0 millimeters), and hole 64C may be sized to accommodate a 7.5 millimeter diameter implant (e.g. hole 64C may have a diameter slightly larger than 7.5 millimeters). Hole 64D may serve the same purpose as identified above with respect to hole 48D. Markings 65 may be placed on a side of arm 24, which may be used to determine or verify the length of an implant, in one particular instance a fixed-axis screw. A hollow or indentation 66 is provided, in one embodiment, in which a hole 67 (which could house a pin or other reference marker) can be placed. The implant is placed in the hollow, e.g. a rounded seat portion is laid in hollow 66, and the length of the implant is read from or verified by reference to markings 65. If the implant includes a protrusion, then the protrusion could be fitted into or adjacent hole 67, and then the length can be read. If the implant has an appropriate hole, and a pin is in hole 67, then such hole in the implant can be placed over or adjacent the pin, and the length of the implant can be read or verified. Of course, it will be understood that other types of markings indicating measurements, configuration, or other information may be placed on arm 24.

Arm 24 further includes a flange 69 that in one embodiment is substantially circular at least in part. Flange 69 has a hole 70, and is sized approximately the same as or slightly smaller than the width of gap 45 of arm 22. Holes 46 through flanges 44 of arm 22 and hole 70 through flange 69 of arm 24, in one embodiment, when substantially aligned form a pivot point 26 for arms 22 and 24. A shoulder screw 73 (described further below) or a pin or other axle is inserted through holes 46 and 70. In embodiments using screw 73 and having at least one threaded hole 46, screw 73 may be threaded into hole 46.

Arm 24 further includes a roughened portion 74 on an inner surface. Roughened portion 74, in one embodiment, includes a series of ridges, which may be V-shaped ridges, or of other configuration. Roughened portion 74 could have other types of roughened surfaces. Roughened portion 74 is provided to allow a surgeon to hold an intervertebral spacer or cage, or other orthopedic device, and/or to pack in or tamp down graft, osteogenic material or other material (e.g. allograft, autograft, or bone morphogenic protein) within the spacer. In a particular embodiment, the length of roughened portion 74 is approximately the same as the length of an opening in a vertebral spacer, so that most or all of roughened portion 74 can be used to pack material into the spacer's opening. In a particular embodiment, instrument 20 can be placed on its side with arms 22 and 24 spread, and a spacer or cage can be placed on roughened portion 74. Graft or other material can be placed in the cage, and arms 22 and 24 can be pressed together to tamp down the material in the cage. Roughened portion 74 could be used for other purposes, such as clamping, crimping, or roughening parts of an orthopedic implant system.

Three disks are connected to arms 22 and 24 in the illustrated embodiment. A large disk 80 has a hole 82 from top to bottom, a substantially cylindrical portion 84, and an annular groove 86. Groove 86 may be of a substantially uniform curvature in cross-section, and is sized and configured so that orthopedic rods or other supporting members can be at least partially within groove 86. Disk 80 is placed over arms 22 and 24, so that hole 82 of disk 80 is substantially collinear with hole 70 of arm 24 and holes 46 of arm 22. In this embodiment, a screw 73 is inserted through hole 82 of disk 80, hole 70 of arm 24 and holes 46 of arm 22, and threaded into a portion of holes 46 of arm 22. In one embodiment, screw 73 has a substantially cylindrical body 88, an upper flange 90, and a lower threaded portion 92, that has a somewhat smaller diameter than that of substantially cylindrical portion 88. Threaded portion 92 will be sized and configured to be threadedly mateable with a threaded portion of hole(s) 46 of arm 22. Screw 73 may include an internal print 94, e.g. an internal hexagonal print, to enable screw 73 to be properly threaded into hole 46. When screw 73 is tightened with respect to hole 46, arms 22 and 24 should be able to pivot about screw 73, and disk 80 should be able to rotate around screw 73. Screw 73 may be tightened enough to allow such rotation without substantial wobble between arms 22 and 24, and without substantial wobble of disk 80 as it rotates around screw 73. In one particular embodiment, disk 80 may have a countersunk portion 96 that can accommodate some or all of flange 90 of screw 73.

Two smaller disks 98, 100 are also provided. As will be seen in the illustrated embodiment, small disks 98, 100 are substantially identical, and therefore for simplicity only disk 98 will be described. Disk 98 has a hole 106 from top to bottom. In some embodiments, a groove similar to groove 86 of disk 80 may be present in one or both of disks 98, 100. Disk 98 is placed on arm 22 so that hole 106 is substantially concentric with hole 47 of arm 22. An axle (e.g. screw 73, described above, or a pin or other axle) is inserted through hole 106 of disk 98 and into hole 47 of arm 22. In an embodiment using screw 73, screw 73 is threaded into threaded portion 47A of hole 47 of arm 22. Similarly, the hole through disk 100 is aligned with hole 63 in arm 24, and an axle (e.g. shoulder screw 73) is inserted through disk 100 and arm 24 and secured into the threaded portion of hole 63 of arm 24. As noted above with respect to disk 80, the axles used with respect to disks 98 and 100 maintain disks 98 and 100 adjacent to arms 22 and 24, respectively, but allow rotation of disks 98 and 100 with respect to arms 22 and 24 without substantial wobbling. In a particular embodiment, disks 98 and/or 100 may have a countersunk portion 108 that can accommodate some or all of flange 90 of screw 73.

The illustrated embodiment of instrument 20 may be used for several different surgical tasks. In the following discussion, the example of surgery on the spine is used. Instrument 20 may be used with other surgical sites, types or techniques.

Instrument 20 may be used as a distractor. The surgeon first obtains access to the surgical site via an opening or other surgical approach. As one example, a midline incision above the affected area is made, and tissue is resected laterally to the transverse process. Pilot holes in vertebrae, e.g. in pedicles, may be made, and implants may be inserted into or otherwise connected to two or more vertebrae. In one embodiment, a support member (for example, a spinal rod) may be connected to the implants, and tightened to one of the implants. Instrument 20 may be inserted to the surgical site. Specifically, end portions 32 and 54 of arms 22 and 24 are moved toward and between the implants to be distracted. The surgeon may manipulate instrument 20 so that a portion of the support is at least partially within one or both of openings 40 and 59 of instrument 20, and so that end portions 32 and 54 abut respective implants. The surgeon forces end portions 34 and 55 toward each other, for example by placing his fingers, hand, or another instrument in or around concave portions 41 and 60, and squeezing them together. Squeezing together end portions 34 and 55 causes arms 22 and 24 to rotate around pivot point 26, in turn causing end portions 32 and 54 to spread apart. Spreading apart portions 32 and 54 causes their adjacent implants also to spread apart, thereby distracting the vertebrae to which the bone screws are attached. When a satisfactory distraction has been accomplished, the surgeon may adjust and tighten or lock one or both implants with respect to a support so as to maintain the vertebrae in the desired position. When distraction is complete and/or the desired position of the vertebrae is maintained to the surgeon's satisfaction, instrument 20 may be removed from the surgical site.

If instrument 20 is to be used as a compressor, access to the surgical site and implantation of implants and support member(s) are performed, as discussed in one example above. End portions 34 and 55 are inserted into the surgical site and are moved toward and to the outside of the implants to be compressed. The surgeon may manipulate instrument 20 so that a portion of the support is at least partially within one or both of openings 43 and 62 of instrument 20, and so that end portions 34 and 55 abut respective implants. Compression is then performed by the surgeon gripping with his hands or with another tool end portions 32 and 54, and in one embodiment concave portions 38 and 57 of instrument 20, and pulling end portions 32 and 54 apart. Pulling end portions 32 and 54 apart causes arms 22 and 24 to pivot around pivot point 26, bringing together end portions 34 and 55 of instrument 20 and thus forcing together in compression the bone screws and the vertebrae to which they are attached. Once a satisfactory compression has been achieved, the surgeon can adjust one or both spinal screws, and can insure that the relative position of the implants and vertebrae are maintained, such as by locking or further tightening one or both implants. Once satisfactory compression has been attained and the positioning is maintained, instrument 20 may be removed from the surgical site.

Instrument 20 may also be used as a rod bender. A support such as a spinal rod or bar, whether circular, square or otherwise in cross-section, may be bent before it is inserted into the surgical site, or it may be bent in situ after connecting it with one or more other spinal implants. In either case, the support and instrument 20 are manipulated so that the support is between disk 80 and at least one of disks 98 and 100. For example, medial portions 36 and 56 of arms 22 and 24 of instrument 20 may be spread from each other, so that a support can be placed between disks 98 and 100 on one side and disk 80 on the other side. The support may be at least partially within groove 86 of disk 80 and similar grooves in disks 98 and/or 100, if such grooves are present. The surgeon then may push end portions 32 and 54 toward each other. Doing so pivots arms 22 and 24 with respect to each other around pivot point 26, in turn causing disk 98 to rotate or pivot generally clockwise around disk 80 and disk 100 to rotate or pivot generally counterclockwise around disk 80. Disks 98 and 100 press against the support on either side of disk 80 to bend the support, with the apex of the bend being generally in contact with or adjacent to disk 80.

In the midst of surgery, the surgeon may wish to measure or verify the dimensions of items to be used in the procedure. As discussed above, instrument 20 can be used to verify lengths or diameters of supports such as spinal plates and implants such as spinal screws. If the surgeon is uncertain as to the dimension of an item, for example if a legend on or associated with the item is obscured or otherwise difficult to read, the surgeon can use instrument 20 to quickly and easily verify that a particular item is of the size he desires.

Further, as also described above embodiments of instrument 20 can be used with intervertebral spacers or cages, or other similar devices. Instrument 20 allows the surgeon to more effectively pack or tamp substances, such as osteogenic materials, medicinal substances, or other therapeutic substances, in such devices. Instrument 20 may be used to hold or transfer a spacer from a preparatory station or phase to the surgical site.

Figure 10:
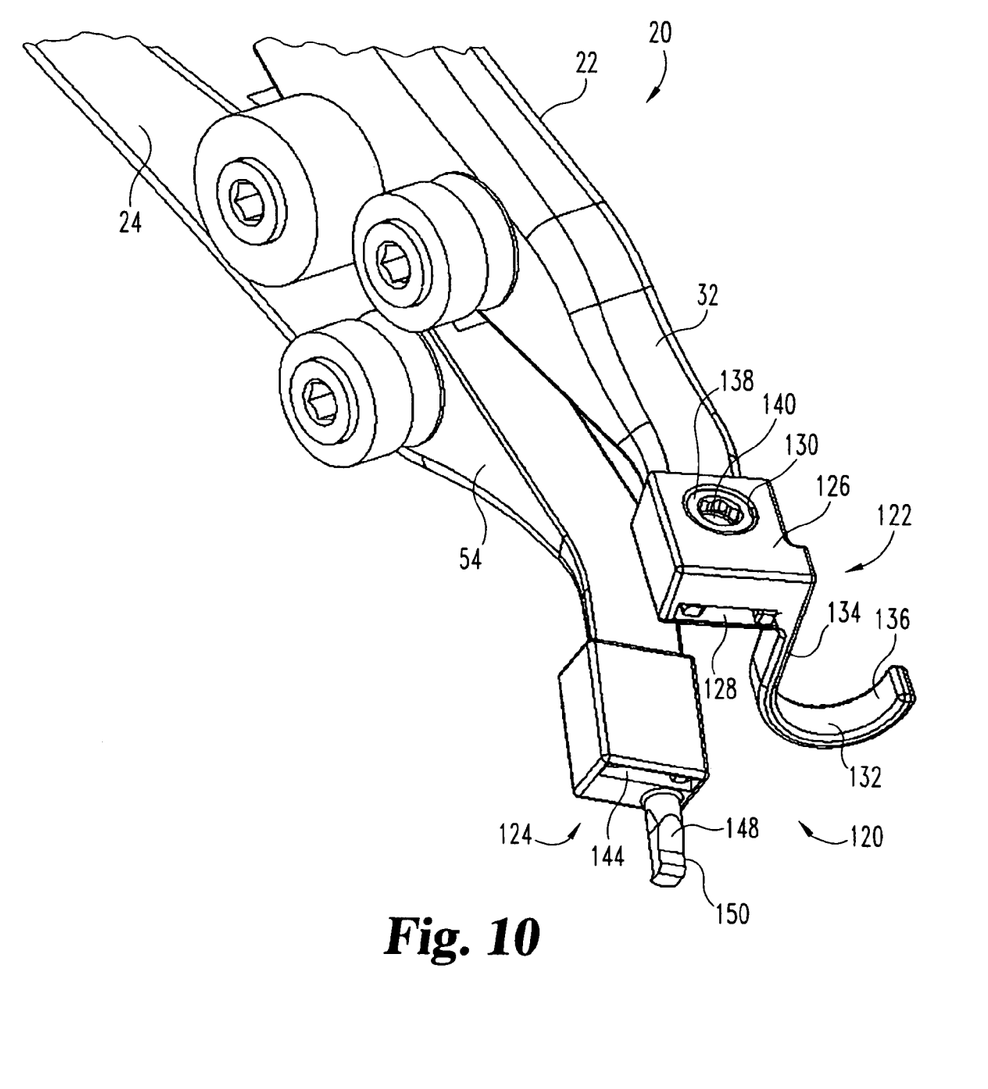
FIG. 10 is a perspective view of the embodiment of FIG. 1 with embodiments of tips.

Embodiments of compressor tips may also be provided. In one embodiment shown generally in FIGS. 10-12, which may be used for example with a spinal plate and bolt implant system, a hook tip 122 connectible to an end portion of an arm of instrument 20, e.g. end portion 34 of arm 22, and an anchor tip 124 connectible to a facing end portion of the other arm, e.g. end portion 55 of arm 24, are provided. Tip 122 has a base 126 with a slot 128 and a hole 130. In the illustrated embodiment, slot 128 extends entirely through base 126. Hole 130 is substantially perpendicular to and communicating with slot 128, may or may not extend entirely through base 126, and is at least partially threaded. Tip 122 further includes a hook 132 connected at one end to base 126. Hook 132 may include a substantially straight portion 134 and a curved portion 136 that in a particular embodiment curves through about 180 degrees. A set screw 138 is also provided, with an internal print 140 (e.g. a hexagonal print), for threading into hole 130. End portion 34 is inserted into slot 128 so that hole 130 is to the outside of arm 22, and set screw 138 is tightened in hole 130 and against a portion of arm 22 so that tip 122 is substantially immobile with respect to arm 22.

In the illustrated embodiment, tip 124 includes a base 142 substantially identical to base 126, including a slot 144 and a hole 146. An extension 148 is connected at one end to base 142. Extension 148 may include one or more notch portions 150 sized and/or configured to accommodate or join with parts of orthopedic implants, such as spinal plate members. A set screw 150, essentially identical to set screw 150, is also provided. End portion 55 of arm 24 is slid into slot 144 of tip 124, and set screw 150 is threaded into hole 146 and against arm 24 so that anchor portion is substantially immobile with respect to arm 24.

Figure 11:
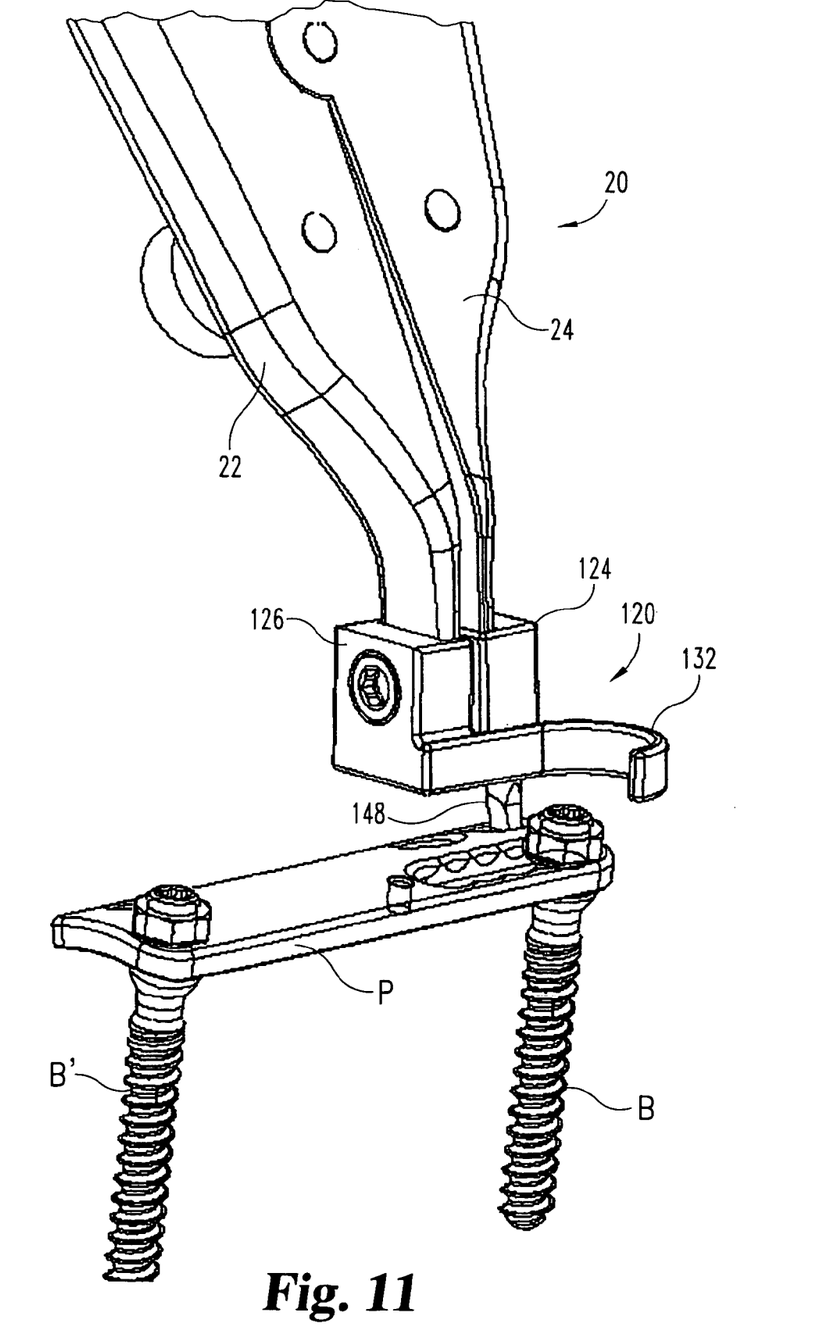
FIG. 11 is a perspective view of the embodiments of FIG. 10 in one embodiment of use.
Figure 12:
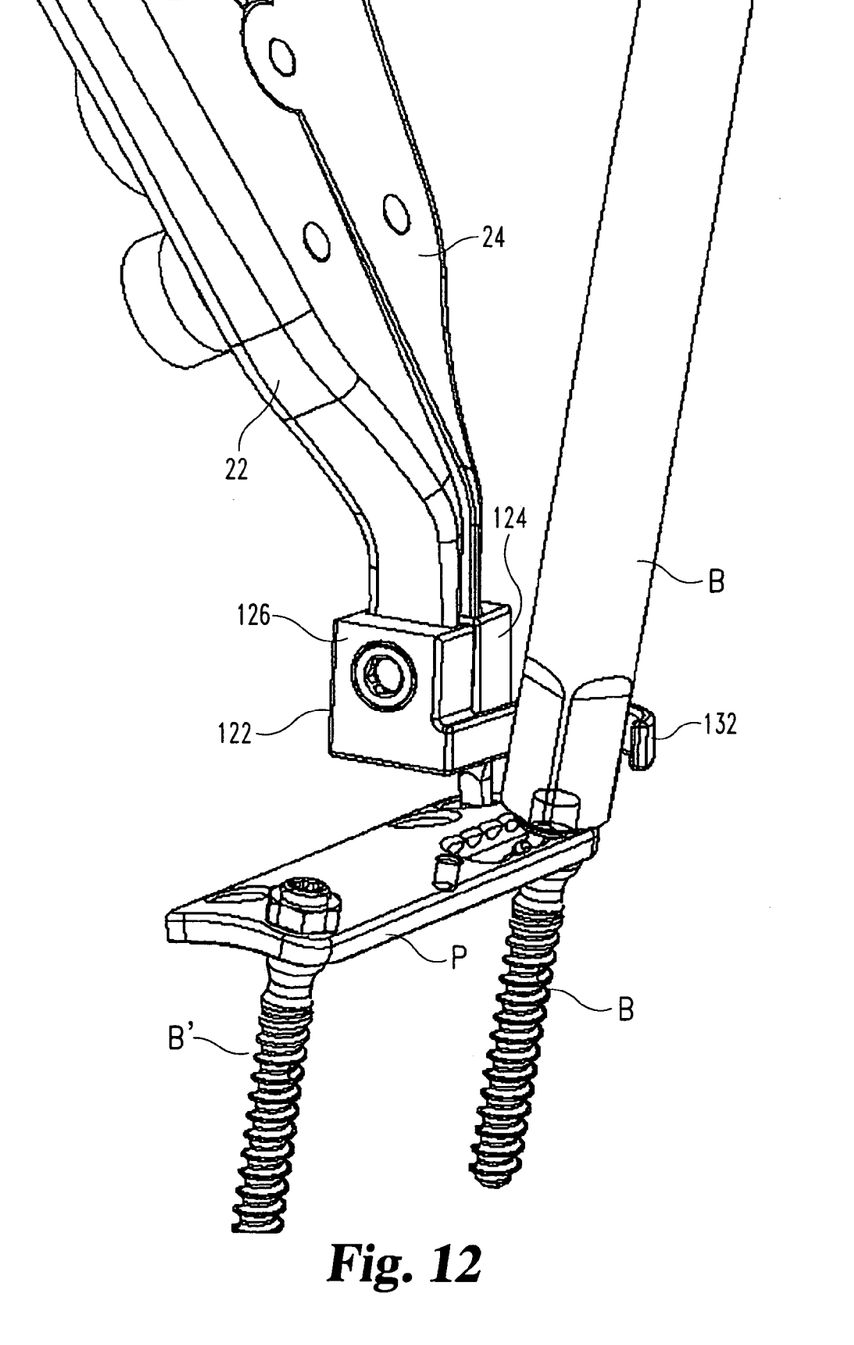
FIG. 12 is a perspective view of the embodiments of FIG. 10 with embodiments of additional structure.

With tips 122 and 124 so connected to instrument 20, and end portions 34 and 55 of instrument 20 abutting or adjacent, instrument 20 can be used, for example, with a spinal plate and bolt construct. As generally shown in FIGS. 11-12, extension 148 can be placed through a hole in plate P so that extension 148 is abutting or adjacent to a side wall of the hole. Hook 132 is placed around a bolt B and/or a driver, holder or other tool T connected to it. Bolt B is engaged to bone tissue, such as a vertebra, through a slot in plate P. Another bolt B' is attached to another vertebra through another hole in plate P. Pushing together end portions 32 and 54 of instrument 20 causes end portions 34 and 55 to spread apart from each other. In so spreading, hook 132 catches bolt B and/or tool T, while extension 148 engages plate P. Such spreading causes bolt B to move with respect to plate P along its slot, and thus to approach bolt B', thereby compressing the vertebrae connected to bolts B and B'.

Figure 13:
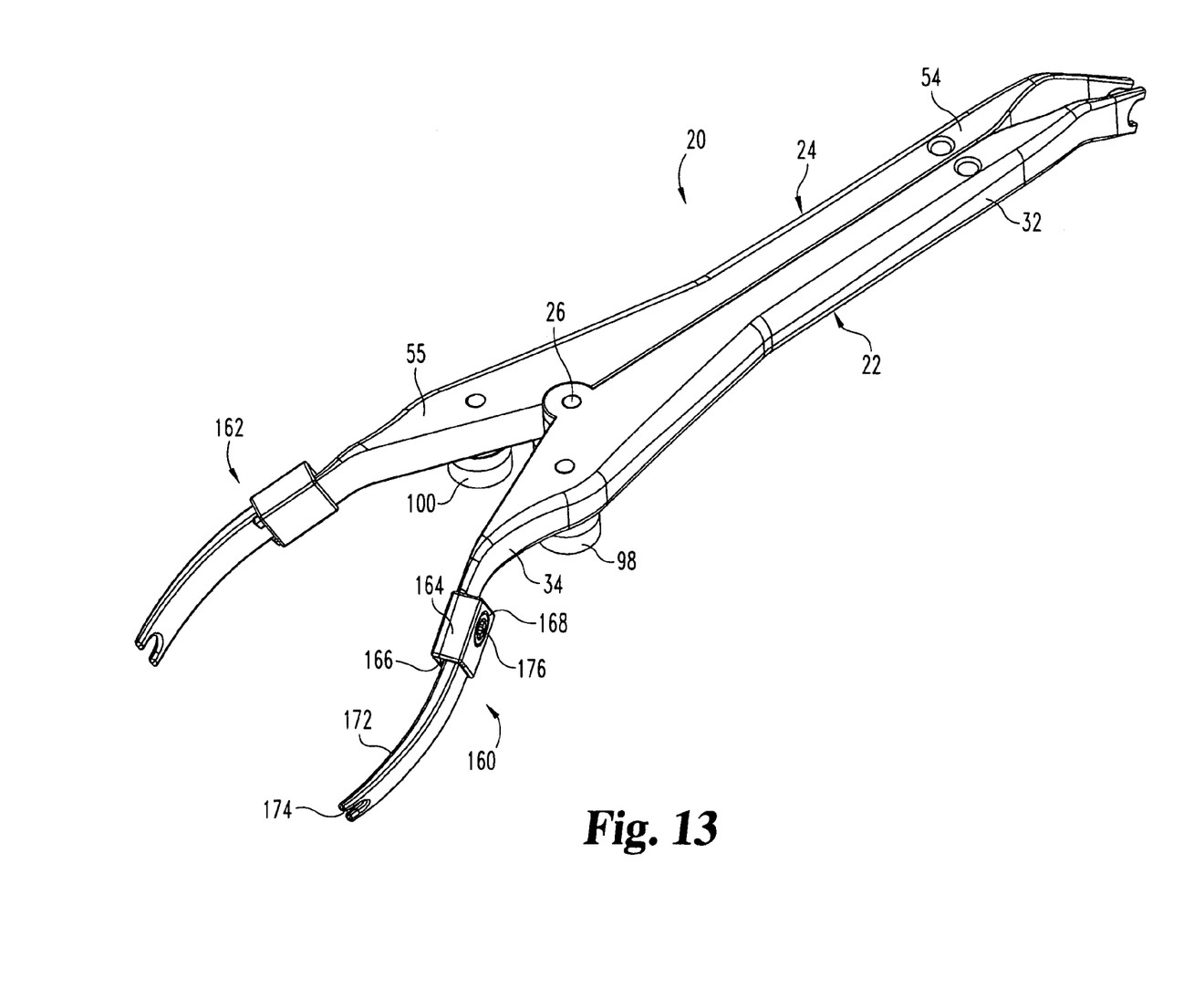
FIG. 13 is a perspective view of the embodiment of FIG. 10 with other embodiments of tips.

In another embodiment, tips 160 and 162 may be placed on the distractor end (e.g. ends 34 and 55) of instrument 20. Tip 160 is connectible to end portion 34 of arm 22, and tip 162 is connectible to end portion 55 of arm 24. Tips 160 and 162 are substantially similar or identical, and therefore they will be described by reference to tip 160. Tip 160 has a base 164 with a slot 166 and a hole 168. In the illustrated embodiment, slot 166 extends entirely through base 164. Hole 168 is substantially perpendicular to and communicating with slot 166, may or may not extend entirely through base 164, and is at least partially threaded. Tip 160 further includes a curved elongated piece 170 connected at one end to base 164. A concave surface 172 generally faces the other tip (e.g. tip 162), and a channel 174 may be provided in an end of piece 170. Channel 174 is U-shaped and sized to accommodate an orthopedic support (e.g. a rod) in the illustrated embodiment. A set screw 176 is also provided, with an internal print (e.g. a hexagonal print), for threading into hole 168. End portion 34 is inserted into slot 164 so that hole 168 is to the outside of arm 22, and set screw 1768 is tightened in hole 168 and against a portion of arm 22 so that tip 160 is substantially immobile with respect to arm 22.

Tip 162 is connected to arm 24 in substantially the same way. Tips 160 and 162 may be placed on instrument 20 prior to or during surgery, depending on the needs of the surgeon. Tips 160 and 162 may be used when compression is necessary over a relatively long distance, for example a long vertebral segment or multiple segments, or when the compressor end (e.g. ends 32 and 54) of instrument 20 do not provide enough mechanical advantage.

Throughout the specification, information has been described relative to spinal orthopedic applications. It will be understood that the structures and acts shown and disclosed herein can be used in a variety of orthopedic situations. Further, the structures described above are preferably made of biocompatible materials, such as stainless steel or other such known materials. It may be desirable to use a material that is capable of sterilization and reuse.

Examples of attributes or features of the embodiments disclosed herein are not to be considered restrictive. For example, features described with respect to one of the disks described above could be found on others of the disks, and features described with respect to one of the arms disclosed above could be found on the other arm.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. An apparatus, comprising:
    a first arm and a second arm pivotally connected together at a pivot point and including a first pair of adjacent ends that converge and an opposite end portion where said first and second arms diverge from one another between said pivot point and a second pair of adjacent ends, said first pair of ends each having a channel at a first tip of said first pair of ends, and said second pair of ends each having a channel at a second tip of said second pair of ends;
    a first disk including an annular groove, sized and configured so that an orthopedic rod can be at least partially within the groove, connected to said first arm; a second disk including an annular groove, sized and configured so that an orthopedic rod can be at least partially within the groove, connected to said second arm; and
    a third disk connected to said arms at approximately the pivot point.

2. The apparatus of claim 1, wherein said arms have medial portions that lie substantially in a plane, and wherein said first pair of ends do not lie in said plane.

3. The apparatus of claim 1, wherein said arms have medial portions that lie substantially in a plane, and wherein said second pair of ends do not lie in said plane.

4. The apparatus of claim 3, wherein said first pair of ends do not lie in said plane, and a first angle between said plane and said second pair of ends and a second angle between said plane and said converging ends are substantially equal.

5. The apparatus of claim 1, wherein at least one of said arms includes a set of ridges facing the other arm.

6. The apparatus of claim 5, wherein said set of ridges is of a length approximately the same as the length of an opening in a bone spacer.

7. The apparatus of claim 1, wherein one of said arms includes a ledge on one side and markings indicating distance to one side of said ledge, whereby placing an implant against said ledge and along said markings indicates the length of the implant.

8. The apparatus of claim 1, wherein at least one of said arms includes a plurality of holes of predetermined diameter generally corresponding to implant diameters and markings indicating implant diameter, whereby finding one of said holes that closely fits an implant verifies the diameter of the implant.

9. The apparatus of claim 1, wherein at least one of said arms includes an indentation and markings indicating distance to one side of said indentation, whereby placing an implant against said indentation and along said markings indicates the length of the implant.

10. The apparatus of claim 9, wherein both of said arms includes an indentation and markings indicating distance to one side of said indentation, one of said arms marked for a multi-axial screw, and the other of said arms marked for a fixed screw, whereby placing an implant against said indentation and along said markings indicates the length of the implant.

11. The apparatus of claim 1, further comprising a pair of tips connected to one of said pairs of adjacent ends, each said tip connected to its respective end via a screw.

12. The apparatus of claim 11, wherein a first of said tips includes a base that connects to a respective end and has a threaded hole for a screw and a hook portion curving generally away from said base; and
    wherein a second of said tips includes a base that connects to a respective end and has a threaded hole for a screw and an anchor portion extending from said base substantially parallel to the end to which said second tip is connected.

13. The apparatus of claim 11, wherein a first of said tips includes a base that connects to a respective end and has a threaded hole for a screw and a curved extension, said extension having a concave surface and a channel at an end distal from said base; and
    wherein a second of said tips includes a base that connects to a respective end and has a threaded hole for a screw and a curved extension, said extension having a concave surface and a channel at an end distal from said base; and
    wherein said concave surfaces of said tips generally face each other.

14. The apparatus of claim 11, wherein each of said tips includes a slot, said tips being connected to said one of said pairs of adjacent ends by insertion of respective ends into respective slots of said tips.

15. The apparatus of claim 1, further comprising a tip having a slot and a threaded hole with a set screw, said tip being connected to one of said ends by insertion of said one of said ends into said slot and locking said set screw against said one of said ends.

16. The apparatus of claim 1, wherein each of said adjacent first pair of ends curves generally inward toward each other, and each of said adjacent second pair of ends point relatively away from each other.

17. The apparatus of claim 1, wherein each of said first pair of ends is monolithic with its respective arm and has an end surface, an inner surface and an outer surface, and said channel extends through said inner and outer surfaces and is open through said end surface, so that a portion of said end surface is on either side of said channel.

18. The apparatus of claim 1, further comprising a spring between said arms.

19. The apparatus of claim 1, wherein at least one of said disks can be rotated with respect to said arms.

20. The apparatus of claim 1, wherein said channels are U-shaped.

21. A multi-use orthopedic apparatus comprising:
    a first arm having a first end, a second end, a medial portion, an inner surface, and an opposite outer surface;
    a second arm having a first end relatively proximate to said first end of said first arm, a second end relatively proximate to said second end of said first arm, a medial portion, an inner surface, and an opposite outer surface, said medial portions of said arms being pivotably connected such that said inner surfaces face one another;
    said first ends tending to converge, and said second ends tending to diverge;
    said inner surfaces at said first ends being at least partially concave, and said outer surfaces at said second ends being at least partially concave;
    a plurality of holes in at least one of said arms, said holes being of various sizes generally corresponding to orthopedic implant sizes, whereby the diameter of a given implant can be verified;
    a ledge positioned on a surface extending between said inner surface and said outer surface of one of said arms and a series of lines generally parallel to said ledge at various distances from said ledge and a plurality of distance indicators associated with said series of lines; and a set of ridges on at least one of said arms, said ridges substantially facing the other of said arms.

22. The apparatus of claim 21 further including a spring between said arms.

23. The apparatus of claim 21, further including a first disk connected to said first arm, a second disk connected to said second arm, and a third disk connected to said arms at the point at which the arms are pivotably connected.

24. The apparatus of claim 23, wherein at least one of said disks can be rotated with respect to said arms.

25. The apparatus of claim 23, wherein said first disk and said second disk each include an annular groove.

26. The apparatus of claim 21, wherein said first ends each have a U-shaped channel.

27. The apparatus of claim 21, wherein said medial portions of said arms lie substantially in a plane, and said first ends of said arms do not lie in said plane.

28. The apparatus of claim 21, wherein said second ends each have a U-shaped channel.

29. The apparatus of claim 21, wherein said medial portions of said arms lie substantially in a plane, and said second ends of said arms do not lie in said plane.

30. An apparatus, comprising:

a first arm and a second arm pivotally connected together at a pivot point and including a first pair of adjacent ends that converge and an opposite end portion where said first and second arms diverge from one another between said pivot point and a second pair of adjacent ends, said first pair of ends each having a channel at a first tip of said first pair of ends, and said second pair of ends each having a channel at a second tip of said second pair of ends;

a first disk including an annular groove, sized and configured so that an orthopedic rod can be at least partially within the groove, connected to said first arm; a second disk including an annular groove, sized and configured so that an orthopedic rod can be at least partially within the groove, connected to said second arm; and a third disk connected to said arms at approximately the pivot point, wherein said disks have centers, and said center of said third disk is nearer to said first pair of ends than a line connecting said centers of said first and second disks.

* * * * *